United States Patent [19]

Gatto

[11] Patent Number: 5,103,054
[45] Date of Patent: Apr. 7, 1992

[54] TERTIARY SULFONAMIDES

[75] Inventor: Vincent J. Gatto, Baton Rouge, La.

[73] Assignee: Ethyl Corporation, Richmond, Va.

[21] Appl. No.: 670,336

[22] Filed: Mar. 15, 1991

Related U.S. Application Data

[63] Continuation-in-part of Ser. No. 518,486, May 3, 1990, abandoned.

[51] Int. Cl.$^5$ ............................................. C07C 311/03
[52] U.S. Cl. ......................................... 564/99; 564/92; 106/186; 252/47.5; 252/402; 524/169; 530/427
[58] Field of Search ............... 564/92, 99; 252/402, 252/47.5; 524/168, 169; 106/186; 530/427

[56] References Cited

U.S. PATENT DOCUMENTS

| | | | |
|---|---|---|---|
| 2,236,168 | 3/1941 | Dietrich | 252/47.5 |
| 3,329,714 | 7/1967 | Martin | 106/186 |
| 3,506,711 | 4/1970 | Tesoro et al. | 106/186 |
| 3,703,487 | 11/1972 | Green et al. | 106/186 |
| 3,780,103 | 12/1973 | Knell | 252/402 |
| 3,927,091 | 12/1975 | Huber-Emden et al. | 252/402 |
| 3,966,194 | 12/1976 | Gencarelli et al. | 564/99 |
| 4,013,621 | 3/1977 | Knell | 564/92 |
| 4,132,702 | 1/1979 | Schmidt et al. | 524/84 |

FOREIGN PATENT DOCUMENTS

| | | | |
|---|---|---|---|
| 033178 | 9/1974 | Japan | 564/92 |
| 7905000 | 3/1980 | Netherlands . | |

*Primary Examiner*—Glennon H. Hollrah
*Assistant Examiner*—Scott C. Rand
*Attorney, Agent, or Firm*—Patricia J. Hogan

[57] ABSTRACT

Tertiary sulfonamides having utility as antioxidants are compounds corresponding to the formula:

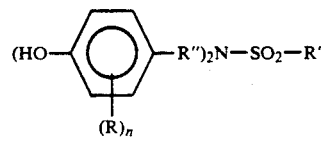

wherein R and R' are independently selected from alkyl, aryl, and benzyl groups, R" is an alkylene group containing 1-5 carbons, and n is an integer of 1-3.

10 Claims, No Drawings

TERTIARY SULFONAMIDES

CROSS-REFERENCE TO RELATED APPLICATION

This application is a continuation-in-part of copending application S. N. 518,486, filed May 3, 1990, now abandoned.

FIELD OF INVENTION

The invention relates to tertiary sulfonamides which are useful as antioxidants.

BACKGROUND

As disclosed in U.S. Pat. Nos. 3,780,103 (Knell), 3,927,091 (Huber-Emden et al.), 3,996,194 (Gencarelli et al.), and 4,132,702, (Schmidt et al.) and Netherlands Patent Application 7905000 (Cincinnati Milacron Chemicals), it is known that some amides containing substituted hydroxyphenyl groups have been found to be useful as stabilizers for organic materials which are normally susceptible to oxidative deterioration.

SUMMARY OF INVENTION

The present invention resides in novel tertiary sulfonamides which are useful as antioxidants. These novel tertiary sulfonamides are compounds corresponding to the formula:

$$(p-HO-C_6R_nH_{4-n}-R'')_2N-SO_2-R'$$

wherein R and R' are independently selected from alkyl, aryl, and benzyl groups, R'' is an alkylene group containing 1-5 carbons, and n is an integer of 1-3.

DETAILED DESCRIPTION

The novel tertiary sulfonamides of the invention are N,N-disubstituted sulfonamides in which the alkyl substituent para to the hydroxy group in each of the N-substituents may have a branched or unbranched chain but is preferably such that the R'' of the formula is a $-(CH_2)_m-$ group in which m is an integer of 1-5, most preferably 2-5.

As indicated by the formula, the novel tertiary sulfonamides may be derivatives of aliphatic or aromatic sulfonamides, although it is generally preferred that they be derivatives of aliphatic sulfonamides, i.e., compounds in which R' of the formula is an alkyl group, most preferably an alkyl group of 1-20 carbons. Also, although the R substituents on the p-hydroxyphenylalkyl groups may be 1-3 in number; may be alkyl, aryl, or benzyl; and, when there is more than one, may be the same or different, it is usually preferred that there be two substituents, which are most commonly alkyl groups containing 1-6 carbons (preferably 1-4 carbons), in the positions ortho to the hydroxy group.

Exemplary of the novel tertiary sulfonamides are the methanesulfonamides, propanesulfonamides, and benzenesulfonamides in which the N-substituents are β-(3,5-di-t-butyl-4-hydroxyphenyl)-ethyl, β-(3-methyl-5-t-butyl-4-hydroxyphenyl)ethyl, β-(3,5-diphenyl-4-hydroxyphenyl)ethyl, β-(3-benzyl-5-methyl-4-hydroxyphenyl)ethyl, β-(3-t-butyl-4-hydroxyphenyl)ethyl, β-(2-methyl-3,5-di-t-butyl-4-hydroxyphenyl)ethyl, β-(3,5-diisopropyl-4-hydroxy-phenyl)ethyl, γ-(3,5-di-t-butyl-4-hydroxyphenyl)propyl, γ-(3-methyl-5-t-butyl-4-hydroxyphenyl)propyl, β-methyl-Y-(3,5-di-t-butyl-4-hydroxyphenyl)propyl, ε-(3-t-butyl-4-hydroxyphenyl)pentyl, or the like.

The preferred tertiary sulfonamides of the invention are N,N-bis[β-(3,5-di-t-butyl-4-hydroxyphenyl)ethyl]methanesulfonamide, N,N-bis[β-(3,5-diisopropyl-4-hydroxyphenyl)ethyl]methanesulfonamide, and N,N-bis[β-(3-methyl-5-t-butyl-4-hydroxyphenyl)ethyl]methanesulfonamide.

The tertiary sulfonamides may be prepared by reacting the appropriate sulfonyl halide corresponding to the formula R'SO₂X with the appropriate secondary amine corresponding to the formula:

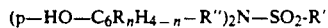

$$(p-HO-C_6R_nH_{4-n}-R'')_2NH$$

X representing halo, preferably chloro or bromo; and R, R', R'', and n being as previously defined. Thus, for example, a sulfonyl halide such as methanesulfonyl chloride, 1-butanesulfonyl bromide, 1-pentanesulfonyl chloride, 1-decanesulfonyl chloride, or benzenesulfonyl chloride is reacted with a secondary amine such as bis[β-(3,5-di-t-butyl-4-hydroxyphenyl)ethyl]amine, bis[γ-(3-methyl-5-t-butyl-4-hydroxyphenyl)propyl]amine, or other such amine.

In the synthesis of the tertiary sulfonamides, the amines and sulfonyl halides are reacted in a mol ratio of about 0.5-1/1, preferably about 0.9/1, in a solvent which is inert to the reaction and which is capable of solubilizing both the reactants and the product and optionally in the presence of an acid scavenger which can neutralize acid produced by the reaction without adversely affecting the process.

Solvents suitable for use in the reaction include, e.g., toluene, benzene, xylene, mesitylene, chlorobenzene, methylene chloride, chloroform, carbon tetrachloride, 1,2-dichloroethane, 1,1,2-trichloroethane, and the like, the preferred solvents usually being toluene and methylene chloride.

Examples of acid scavengers which may be used in the process are triethylamine, tripropylamine, tributylamine, pyridine, and the like, with the preferred acid scavenger being triethylamine. When employed, the acid scavenger is used in an amount such as to provide about one mol of acid scavenger per mol of acid generated by the reaction.

In the preparation of the tertiary sulfonamides, the components of the reaction mixture are combined in any suitable way, conveniently by adding a solution of the amine (and optionally also an acid scavenger) in a portion of the solvent to a solution of the sulfonyl halide in the remainder of the solvent over a period of about 0.5-1 hour while maintaining the reaction mixture at a temperature of about 0°-25° C. Then, when combination of the reactants is at least substantially complete, the temperature is raised, if necessary, to be in the range of about 10°-45° C., preferably about 25°-35° C., and kept in that range for about 2-10 hours. It is ordinarily most convenient in this reaction to use ambient temperature.

After completion of the reaction, the product can be recovered in any suitable way. For example, the reaction mixture may be diluted with solvent, preferably the same solvent as was used in the reaction; the diluted reaction mixture may then be washed with an inorganic acid, such as HCl; the organic phase resulting from this wash may be recovered and washed with a base, such as NaOH; the organic phase resulting from this wash may be recovered and washed with a salt solution, e.g., aqueous NaCl; and the organic phase resulting from this wash may be recovered and dried to yield the desired tertiary sulfonamide.

The tertiary sulfonamides of the invention are especially useful as antioxidants for organic materials which are normally susceptible to oxidative deterioration, such as the organic materials taught in Knell, Huber-Emden et al., Gencarelli et al., and Schmidt et al., the teachings of all of which are incorporated herein by reference. They are particularly useful in this regard when used to stabilize olefin polymers and copolymers, e.g., polyethylene, polypropylene, etc.

When used as antioxidants, the tertiary sulfonamides may be employed as the sole stabilizers for the normally-oxidizable organic materials, or they may be used in conjunction with other stabilizers, such as conventional phenolic antioxidants, thioester synergists, etc. Moreover, their activity as antioxidants does not appear to be inhibited by the presence in the organic materials of additives such as those conventionally employed in such materials, e.g., light stabilizers, ultraviolvet light absorbers, metal deactivators, pigments, dyes, lubricants, nucleating agents, fillers, and the like.

The following examples are given to illustrate the invention and are not intended as a limitation thereof. Unless otherwise specified, quantities mentioned in the examples are quantities by weight.

EXAMPLE I

Charge a suitable reaction vessel with 2.9 g of methanesulfonyl chloride and 10 mL of dry toluene. While stirring the reaction mixture and maintaining the temperature at 0°-8° C., slowly add a solution of 9 g of bis[$\beta$-(3,5-di-t-butyl-4-hydroxyphenyl)ethyl]-amine, 2.7 g of triethylamine, and 30 mL of dry toluene. Then allow the reaction mixture to reach ambient, i.e., room, temperature, and maintain that temperature for four hours.

After completion of the four-hour period, wash the reaction mixture consecutively with 50 mL of 3N HCl, 50 mL of 1N NaOH, and 50 mL of a saturated aqueous NaCl solution, the organic phase being recovered after each wash and then subjected to the next wash. Recover the final washed organic phase, dry, and concentrate in vacuo to provide a crude product containing 97.6 area % of N,N-bis[$\beta$-(3,5-di-t-butyl-4-hydroxyphenyl)ethyl]methanesulfonamide.

Recrystallize the crude product from 100 mL of heptane. GC analysis shows the recrystallized product to contain >99% of the tertiary sulfonamide, which has a melting point of 132°-134° C. Spectral analyses (H-NMR, $^{13}$C-NMR, IR, GC-MS) confirm the identity of the solid as N,N-bis[$\beta$-(3,5-di-t-butyl-4-hydroxyphenyl)ethyl]methanesulfonamide.

EXAMPLE II

Part A

Prepare a blend of polypropylene and 0.05% of calcium stearate as a lubricant. Retain an aliquot of the blend as a control (Blend A) and modify another aliquot by blending 0.1% of the product of Example I as an antioxidant to form Blend B.

Part B

Test the compositions of Part A for melt flow index by extruding them in a Brabender twin screw extruder at 150°-245°-245° C. and 30 rpm under nitrogen and then making five passes through a Brabender single screw extruder at 260°-260°-260°-260° C. and 30 rpm with ambient air. The test results are shown below.

| Blend | MFI @ 230° C./2160 g Load Extrusion Passes | | | |
|---|---|---|---|---|
| | TwS | ss1 | ss3 | ss5 |
| A | 9.6 | 28.5 | 96.5 | — |
| B | 4.3 | 6.1 | 8.4 | 10.9 |

What is claimed is:

1. A tertiary sulfonamide corresponding to the formula:

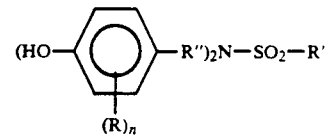

wherein R and R' are independently selected from alkyl, hydrocarbyl, aryl, and benzyl groups, R" is an alkylene group containing 1-5 carbons, and n is an integer of 1-3.

2. The tertiary sulfonamide of claim 1 wherein R is an alkyl group of 1-6 carbons.

3. The tertiary sulfonamide of claim 2 wherein R is an alkyl group of 1-4 carbons.

4. The tertiary sulfonamide of claim 3 wherein R is t-butyl.

5. The tertiary sulfonamide of claim 1 wherein n is 2.

6. The tertiary sulfonamide of claim 1 wherein R" is $(CH_2)_m$ in which m is an integer of 1-5.

7. The tertiary sulfonamide of claim 1 wherein R' is an alkyl group of 1-20 carbons.

8. The tertiary sulfonamide of claim 7 wherein R' is methyl.

9. The tertiary sulfonamide of claim 1 wherein R is an alkyl group of 1-4 carbons, n is 2, R" is $(CH_2)_m$ in which m is an integer of 1-5, and R' is an alkyl group of 1-20 carbons.

10. The tertiary sulfonamide of claim 9 which is N,N-bis[$\beta$-(3,5-di-t-butyl-4-hydroxyphenyl)ethyl]methanesulfonamide.

* * * * *